US010576151B2

(12) United States Patent
Chatzistamou et al.

(10) Patent No.: US 10,576,151 B2
(45) Date of Patent: Mar. 3, 2020

(54) CICLOPIROX FOR USE IN MODULATION OF GLUCOSE HOMEOSTASIS

(71) Applicant: UNIVERSITY OF SOUTH CAROLINA, Columbia, SC (US)

(72) Inventors: Ioulia Chatzistamou, Irmo, SC (US); Hippokratis Kiaris, Irmo, SC (US); Chrysovalantou Mihailidou, Marousi (GR)

(73) Assignee: University of South Carolina, Columbia, SC (US)

( * ) Notice: Subject to any disclaimer, the term of this patent is extended or adjusted under 35 U.S.C. 154(b) by 213 days.

(21) Appl. No.: 15/264,704

(22) Filed: Sep. 14, 2016

(65) Prior Publication Data

US 2017/0071925 A1 Mar. 16, 2017

Related U.S. Application Data

(60) Provisional application No. 62/218,022, filed on Sep. 14, 2015.

(51) Int. Cl.
*A61K 31/4418* (2006.01)
*A61K 45/06* (2006.01)

(52) U.S. Cl.
CPC .................................. *A61K 45/06* (2013.01)

(58) Field of Classification Search
CPC ................................................ A61K 31/4418
See application file for complete search history.

(56) References Cited

PUBLICATIONS

Mayo Clinic. "Type 1 diabetes." © Jan. 17, 2014. Available from: < http://web.archive.org/web/20140117044841/http://www.mayoclinic.org/diseases-conditions/type-1-diabetes/basics/treatment/con-20019573?p=1 >.*
Type I diabetes. © Jan. 22, 2014. Available from: < http://web.archive.org/web/20140122120801/http://www.diabetes.org/diabetes-basics/type-1/ >.*
"Facts about Type 2." © Jan. 20, 2014. Available from: < http://www.diabetes.org/diabetes-basics/type-2/facts-about-type-2.html? >.*
"Medication." © Feb. 16, 2014. Available from: < http://web.archive.org/web/20140216105056/http://www.diabetes.org/living-with-diabetes/treatment-and-care/medication >.*
Lublin, A., et al. "FDA-Approved Drugs that Protect Mammalian Neurons from Glucose Toxicity Slow Aging Dependent on Cbp and Protect Against Proteotoxicity." PLoS One. (Nov. 2011), vol. 6, Issue 11, pp. 1-10.*
American Diabetes Association. "Five Things You Should Know About Prediabetes." (Jul. 29, 2011). Accessed Jul. 5, 2018. Available from: < http://diabetesstopshere.org/2011/07/29/five-things-you-should-know-about-prediabetes/ >. (Year: 2011).*
Norman, J. Endocrineweb. "Managing Diabetes with Blood Glucose Control." Accessed Jul. 5, 2018. (May 27, 2014). Available from: < https://www.endocrineweb.com/conditions/diabetes/assessing-how-well-diabetes-controlled >. (Year: 2014).*
American Diabetes Association. "How to Treat Gestational Diabetes." (Apr. 29, 2014). Accessed Jul. 5, 2018. Available from: < http://www.diabetes.org/diabetes-basics/gestational/how-to-treat-gestational>. (Year: 2014).*
Diabetes.co.uk. "Differences Between Type 1 and Type 2." (Jun. 30, 2015). Accessed Jul. 5, 2018. Available from: < https://www.diabetes.co.uk/difference-between-type1-and-type2-diabetes.html >. (Year: 2015).*
Pharmacy Tech Study. "Dosage Forms / Routes of Administration." (Oct. 14, 2010). Accessed Jul. 5, 2018. Available from: < https://www.pharmacy-tech-study.com/dosage-forms.html >. (Year: 2010).*
FDA. "Diabetes Medicines." (Feb. 19, 2015). Accessed Jul. 5, 2018. Available from: < https://www.fda.gov/downloads/forconsumers/byaudience/forwomen/freepublications/ucm434878.pdf >. (Year: 2015).*
"Design Novel Dual Agonists for Treating Type-2 Diabetes by Targeting Peroxisome Proliferator-Activated Receptors with Core Hopping Approach." PLoS One. (Jun. 7, 2012). vol. 7, Issue 6, pp. 1-9. Accessed Jul. 5, 2018. Available from: < http://journals.plos.org/plosone/article/file?id=10.1371/>. (Year: 2012).*
Diabetes.co.uk. "Incretin Mimetics (GLP-1 Agonists)." (Jul. 5, 2013). Accessed Jul. 5, 2018. Available from: < https://www.diabetes.co.uk/diabetes-medication/incretin-mimetics.html >. (Year: 2013).*
Diabetes.co.uk. "Analogue Insulin." (Jan. 16, 2011). Accessed Jul. 5, 2018. Available from: < https://www.diabetes.co.uk/insulin/analogue-insulin.html >. (Year: 2011).*
Joslin Diabetes Center. "Goals for Blood Glucose Control." (Mar. 28, 2013). Accessed Oct. 30, 2018. Available from: < https://web.archive.org/web/20130328093138/https://www.joslin.org/info/Goals-for-Blood-Glucose-Control.html > . (Year: 2013).*
"Guidelines for Timely Administration of Scheduled Medications (Acute)." (Jan. 12, 2011). Accessed Oct. 30, 2018. Available from: < https://www.ismp.org/guidelines/timely-administration-scheduled-medications-acute > . (Year: 2011).*
Lesson 4: Calculations used to determine patient-specific doses "The right dose". (Feb. 1, 2001). Accessed Oct. 30, 2018. Available from: < http://courses.washington.edu/pharm309/calculations/Lesson4.pdf > . (Year: 2001).*
Kirkman, M.S., et al. "Diabetes in Older Adults." Diabetes Care. (Dec. 2012), vol. 35, pp. 2650-2664. (Year: 2012).*
Lublin, A., et al. "FDA-Approved Drugs that Protect Mammalian Neurons from Glucose Toxicity Slow Aging Dependent on Cbp and Protect Against Proteotoxicity." PLoS One. Accessed Jul. 5, 2018. (Nov. 2011), vol. 6, Issue 11, pp. 1-10. (Year: 2011).*
Back, Sung Hoon, and Randal J. Kaufman "Endoplasmic reticulum stress and type 2 diabetes." Annual review of biochemistry 81 (2012): 767-793.

(Continued)

*Primary Examiner* — Noble E Jarrell
*Assistant Examiner* — John S Kenyon
(74) *Attorney, Agent, or Firm* — Dority & Manning, P.A.

(57) ABSTRACT

Modulation of glucose homeostasis by administration of ciclopirox (6-cyclohexyl-1-hydroxy-4-methylpyridin-2 (1H)-one) is described. Methods can be utilized in treatment of conditions that involve loss of glucose homeostasis, such as diabetes, and in one particular embodiment type II diabetes. Ciclopirox is shown to stimulate p21 expression by mechanisms that are likely p53-independent.

18 Claims, 9 Drawing Sheets

(56) References Cited

PUBLICATIONS

Papa, Feroz R. "Endoplasmic reticulum stress, pancreatic β-cell degeneration, and diabetes." Cold Spring Harbor perspectives in medicine 2.9 (2012): a007666.
Mihailidou, Chrysovalantou, et al. "CHOP-dependent regulation of p21/waf1 during Er stress." Cellular Physiology and Biochemistry 25.6 (2010): 761-766.
Dioufa, Nikolina, et al. "p53 antagonizes the unfolded protein response and inhibits ground glass hepatocyte development during endoplasmic reticulum stress." Experimental Biology and Medicine 237.10 (2012): 1173-1180.
Vassilev LT, Vu BT, Graves B, Carvajal D, Podlaski F, Filipovic Z, Kong N, Kammlott U, Lukacs C, Klein C, Fotouhi N. In vivo activation of the p53 pathway by small-molecule antagonists of MDM2. Science. Feb. 6, 2004;303(5659):844-8.
Mihailidou, Chrysovalantou, et al. "Regulation of P21 during diabetes-associated stress of the endoplasmic reticulum." Endocrine-related cancer 22.2 (2015): 217-228.
Mkrtchian, Souren. "Targeting unfolded protein response in cancer and diabetes." Endocrine-related cancer 22.3 (2015): C1-C4.
Secchiero P, Toffoli B, Melloni E, Agnoletto C, Monasta L, Zauli G. The MDM2 inhibitor Nutlin-3 attenuates streptozotocin-induced diabetes mellitus and increases serum level of IL-12p40. Acta diabetologica. Dec. 1, 2013;50(6):899-906.
Mlynarczyk C, Fåhraeus R. Endoplasmic reticulum stress sensitizes cells to DNA damage-induced apoptosis through p53-dependent suppression of p21(CDKN1A). Nat Commun.2014;5 5067.
Ma TC, Langley B, Ko B, Wei N, Gazaryan IG, Zareen N, Yamashiro DJ, Willis DE, Ratan RR. A screen for inducers of p21waf1/cip1 identifies HIF prolyl hydroxylase inhibitors as neuroprotective agents with antitumor properties. Neurobiol. Dis. 2013;49(1):13-21.
Linden T, Katschinski DM, Eckhardt K, Scheid A, Pagel H, Wenger RH. The antimycotic ciclopirox olamine induces HIF-1alpha stability, VEGF expression, and angiogenesis. FASEB J. 2003;17(6):761-763.
Wanner RM, Spielmann P, Stroka DM, Camenisch G, Camenisch I, Scheid A, Houck DR, Bauer C, Gassmann M, Wenger RH. Epolones induce erythropoietin expression via hypoxia-inducible factor-1 alpha activation. Blood 2000;96(4):1558-1565.
Zhou H, Shen T, Luo Y, Liu L, Chen W, Xu B, Han X, Pang J, Rivera CA, Huang S. The antitumor activity of the fungicide ciclopirox. Int. J. Cancer 2010;127(10):2467-2477.
Minden MD, Hogge DE, Weir SJ, Kasper J, Webster DA, Patton L, Jitkova Y, Hurren R, Gronda M, Goard CA, Rajewski LG, Haslam JL, Heppert KE, Schorno K, Chang H, Brandwein JM, Gupta V, Schuh AC, Trudel S, Yee KWL, Reed GA, Schimmer AD. Oral ciclopirox olamine displays biological activity in a phase I study in patients with advanced hematologic malignancies. Am. J. Hematol. 2014;89(4):363-368.
Mihailidou C, Chatzistamou I, Papavassiliou AG, Kiaris H. Improvement of chemotherapeutic drug efficacy by endoplasmic reticulum stress. Endocr Relat Cancer. 2015;22(2):229-38. doi: 10.1530/ERC-15/0019.
Yang J, Zhang W, Jiang W, Sun X, Han Y, Ding M, Shi Y, Deng H. P21cip-overexpression in the mouse β?? cells leads to the improved recovery from streptozotocin-induced diabetes. PLoS One 2009;4(12). doi:10.1371/journal.pone.0008344.
Bonnefont-Rousselot, Dominique. "Glucose and reactive oxygen species." Current Opinion in Clinical Nutrition & Metabolic Care 5.5 (2002): 561-568.
Yu T, Jhun BS, Yoon Y. High-glucose stimulation increases reactive oxygen species production through the calcium and mitogen-activated protein kinase-mediated activation of mitochondrial fission. Antioxid. Redox Signal. 2011;14(3):425-437.
Swaminathan SI, Fonseca VA, Alam MG, Shah SV. The role of iron in diabetes and its complications Diabetes Care. 2007;30(7):1926-33.
Huang J, Jones D, Luo B, Sanderson M, Soto J, Abel ED, Cooksey RC, McClain DA. Iron overload and diabetes risk: A shift from glucose to fatty acid oxidation and increased hepatic glucose production in a mouse model of hereditary hemochromatosis. Diabetes 2011;60(1):80-87.
Cheng K, Ho K, Stokes R, Scott C, Lau SM, Hawthorne WJ, O'Connell PJ, Loudovaris T, Kay TW, Kulkarni RN, Okada T, Wang XL, Yim SH, Shah Y, Grey ST, Biankin AV, Kench JG, Laybutt DR, Gonzalez FJ, Kahn CR, Gunton JE. Hypoxia-inducible factor-1alpha regulates beta cell function in mouse and human islets. J. Clin. Invest. 2010;120(6):2171-2183.
Erion KA, Ferrante T, Corkey B and Deeney J. Iron stimulates insulin secretion in clonal pancreatic β-cells and dissociated rat islets. FASEB J. 2013;27:1010.13.
Sato, E., Kohno, M., Nakashima, T. And Niwano, Y. Ciclopirox olamine directly scavenges hydroxyl radical. Int J Dermatol. 2008;47:15-18.
Ko, Sae Hee, et al. "Antimycotic ciclopirox olamine in the diabetic environment promotes angiogenesis and enhances wound healing." PloS one 6.11 (2011): e27844.

\* cited by examiner

CICLOPIROX FOR USE IN MODULATION OF GLUCOSE HOMEOSTASIS

CROSS REFERENCE TO RELATED APPLICATION

This application claims filing benefit of U.S. Provisional Patent Application Ser. No. 62/218,022 having a filing date of Sep. 14, 2015, which is incorporated herein by reference in its entirety.

BACKGROUND

Glucose homeostasis describes the body's balance of insulin and glucagon that maintains blood glucose levels and is crucial in maintaining appropriate energy and metabolic state. The inability to maintain glucose homeostasis in both chronic hyperglycemia and hyperlipidemia, known as important causative factors of type 2 diabetes, has been found to disrupt homeostasis of the endoplasmic reticulum (ER) in insulin producing β cells of the pancreatic islets. Given the functional importance of the ER, an organelle that performs folding, modification, and trafficking of secretory and membrane proteins to the Golgi compartment, the maintenance of ER homeostasis in β cells is very important.

Research suggests that ER stress and resulting loss of ER homeostasis is intrinsic to the pathogenesis of diabetes by mechanisms that involve the unfolded protein response. When ER homeostasis is disrupted, the ER generates adaptive signaling pathways, called the unfolded protein response, in an attempt to restore homeostasis. However, if homeostasis fails to be restored, as can occur in chronic ER stress conditions found in diabetes, the ER initiates death signaling pathways (apoptosis). Evidence is growing that the single branches of the unfolded protein response work in concert in β cells to supply insulin in response to acute glucose availability. ER stress due to chronic glucose stimulation disrupts these primarily adaptive changes into an overwhelming unfolded protein response, which leads to reduced insulin supply and loss of β-cell mass due to apoptosis. Accordingly, alleviation of the pro-apoptotic activity of ER stress during diabetes emerges as a strategy of choice in treatment.

It has previously been reported that deregulation of p53/p21 activity occurs during ER stress and is associated with the cytotoxic effects of the unfolded protein response. p21 is a potent cyclin-dependent kinase inhibitor that binds to and inhibits the activity of cyclin-CDK2, -CDK1, and -CDK4/6 complexes, and thus functions as a regulator of cell cycle progression at G1 and S phase. The expression of p21 is tightly controlled by the tumor suppressor protein p53. In the context of diabetes it has been found that stimulation of p53/p21 activity by nutlin-3a (a cis-imidazoline analog activator of p53 stability) is beneficial for diabetes in mice. The specific suppression of p21 during ER stress and its pro-survival activity during DNA damage-induced apoptosis have also been suggested.

Unfortunately, p53 stabilization by nutlin-3a also elicits pro-apoptotic effects that may likely compromise its beneficial activities for diabetes management. This suggests that bypassing the death-inducing function of p53 while inducing the activity of p21 may bear significant anti-diabetic value. Consistent with this notion, p21-deficient diabetic mice have been found to be unresponsive to nutlin-3a and more sensitive to diet-induced diabetes than their wild type counterparts. This is in line with the concept that in the absence of p21, the pro-apoptotic effects of p53 persist, reducing islets' survival and function during treatment of diabetic mice with nutlin-3a.

What are needed in the art are compounds that can encourage pancreatic islet health and survival of β cells in high ER stress conditions such as chronic loss of glucose homeostasis common in diabetes. For instance, a compound that can modulate the unfolded protein response in conditions of high ER stress and thus modulate glucose homeostasis could be of great benefit.

SUMMARY

According to one embodiment, disclosed is a method of modulating glucose homeostasis through utilization of ciclopirox (CPX). For instance, a method can include administrating CPX to a subject in need thereof, e.g., a person diagnosed with diabetes.

BRIEF DESCRIPTION OF THE DRAWINGS

A full and enabling disclosure of the present invention, including the best mode thereof, directed to one of ordinary skill in the art, is set forth in the specification, which makes reference to the appended figure, in which:

FIG. 8 illustrates pancreatic islet morphology (H&E staining) of wild type non-diabetic (upper panel) or diabetic (lower panel) mice receiving CPX or saline (A). Arrows show islets. FIG. 8 also presents the quantification of islet numbers expressed as % vs. control non-diabetic mice (B). *–$P<0.05$; **–$P<0.005$ Student's T test.

DETAILED DESCRIPTION

The following description and other modifications and variations to the present invention may be practiced by those of ordinary skill in the art, without departing from the spirit and scope of the present disclosure. In addition, it should be understood that aspects of the various embodiments may be interchanged in whole and in part. Furthermore, those of ordinary skill in the art will appreciate that the following description is by way of example only, and is not intended to limit the invention.

In general, disclosed herein is a method for modulating glucose homeostasis. More specifically, disclosed methods can be used for treating conditions that involve loss of glucose homeostasis, such as diabetes, and in one particular embodiment type II diabetes, by use of Ciclopirox (CPX). CPX (IUPAC name: 6-cyclohexyl-1-hydroxy-4-methylpyridin-2(1H)-one; Trade name: Loprox) is an iron chelator that in addition to the stimulation of p21 expression can also cause accumulation of HIF1 transcription factor in the nucleus. HIF1 is the master regulator of oxygen homeostasis that stimulates angiogenesis at conditions of limited oxygen supply and CPX has been shown to stimulate HIF-1-dependent gene expression. CPX has also been shown to possess antitumor activity by mechanisms that are likely p53-independent.

According to the present disclosure, it has been found that CPX possesses anti-diabetic activity that is associated with its ability to modulate the intensity of ER stress. Without wishing to be bound to any particular theory, and as described further in the Examples section, below, CPX is shown herein to be an activator of p21 expression that operates independently of p53 stabilization and thus possesses excellent characteristics for modulating the unfolded protein response while avoiding the pro-apoptotic effects of p53.

In vitro, CPX can protect islets from high glucose-induced glucotoxicity and can effectively restore glucose levels in diabetic subjects in vivo. CPX can have little effect on glucose levels in non-diabetic subjects implying that this pharmacological agent can be particularly efficient during ER stress. Beneficially, CPX can suppress the expression of ER stress markers BiP, GRP94 and CHOP and can reduce the levels of reactive oxygen species during culture at high glucose. The reduction of ER stress is believed to be associated with the ability of CPX to inhibit insulin release. Iron citrate can stimulate insulin release, and this can be inhibited by CPX, which is known to function as iron chelator. It is believed that inhibition of insulin production constrains ER stress in islets thereby promoting their survival. This unfolded protein response-antagonizing activity of CPX suggests application for the management not only of diabetes, but other conditions related to ER stress.

In some embodiments, CPX can be administered to a subject afflicted with diabetes, including but not limited to type I diabetes, type II diabetes, gestational diabetes, and pre-diabetes. Utilization of CPX as disclosed herein is not limited to treatment of diabetes, however, and can be utilized in treatment of other metabolic conditions that lead to loss of glucose homeostasis and overwhelming of the unfolded protein response. Through treatment including administration of CPX the blood sugar level of a subject afflicted with loss of glucose homeostasis can be improved or maintained. The blood sugar concentration in the blood in healthy individuals is normally maintained between 64.8 and 104,4 mg/dL (American Diabetes Association, "Standards of Medical Care in Diabetes—2010", *Diabetes Care*, 33: S1-S61, 2010).

In one embodiment, modulation of glucose homeostasis through utilization of CPX administration may be carried out for an elderly subject, e.g., an individual of about 60 years of age or greater, about 65 years of age or greater, or about 70 years of age or greater in some embodiments. Without wishing to be bound to any particular theory, the beneficial activity of CPX in glucose homeostasis may be particularly relevant for the elderly due to deregulation of the unfolded protein response as well as deregulation of p21 during aging.

As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of disease as the individual being treated, who is about the same age as the individual being treated (to ensure that the stages of the disease in the treated individual and the control individual(s) are comparable).

Type I diabetes is an auto-immune disease that affects the islets of Langerhans, destroying the body's ability to produce insulin. Type I diabetes represents 10% of all diabetes cases and affects as many as 1 million people in the United States. Type II diabetes is a metabolic disorder resulting from the body's inability to produce enough insulin or properly use the insulin produced. Roughly 90% of all diabetic individuals in the United States suffer from type II diabetes. Other, less common forms of diabetes that can be treated as described herein include gestational diabetes, in which pregnant women who have never had diabetes before have a high blood glucose level during pregnancy; monogenic diabetes, which behaves similarly to Type 1 diabetes and is caused by a single gene mutation; congenital diabetes, which is due to genetic defects of insulin secretion; cystic fibrosis-related diabetes; and steroid diabetes induced by high doses of glucocorticoids.

Treatment of diabetes by use of CPX, optionally in conjunction with other diabetes treatment protocols, can modulate glucose homeostasis thereby regulating blood sugar levels that are responsible for most of the symptoms associated with diabetes. Diabetes associated symptoms include, but are not limited to polyuria (frequent urination), polydipsia (increased thirst), polyphagia (increased hunger). Prolonged high blood glucose can cause glucose absorption in the lens of the eye, which leads to changes in its shape, resulting in vision changes. A number of skin rashes which can occur in diabetes are collectively known as diabetic dermadrornes. Long term complications of diabetes include damage to the blood vessels. For instance, diabetes doubles the risk of cardiovascular disease, The main "macrovascular" diseases (related to atherosclerosis of larger arteries) are ischemic heart disease (angina and myocardial infarction), stroke and peripheral vascular disease. Diabetes also causes "microvascular" complications—damage to the small blood vessels. Diabetic retinopathy, which affects blood vessel formation in the retina of the eye, can lead to visual symptoms, reduced vision, and potentially blindness. Diabetic nephropathy, the impact of diabetes on the kidneys, can lead to scarring changes in the kidney tissue, loss of small or progressively larger amounts of protein in the urine, and eventually chronic kidney disease requiring dialysis. Diabetic neuropathy is the impact of diabetes on the nervous system, most commonly causing numbness, tingling and pain in the feet and also increasing the risk of skin damage due to altered sensation. Together with vascular disease in the legs, neuropathy contributes to the risk of diabetes-related foot problems (such as diabetic foot ulcers) that can be difficult to treat and occasionally require amputation.

In some embodiments, CPX can be used for reducing risk of diabetes and thus may be administered as a prophylactic in some embodiments, Risk factors associated with diabetes in general, and with the development of type II diabetes in particular, include a family history of diabetes, belonging to certain ethnic or racial groups, a history of gestational diabetes, obesity, in particular, high levels of visceral or abdominal fat, a sedentary lifestyle, age, high blood pressure, schizophrenia, as well as altered glucose metabolism, including impaired glucose tolerance or pre-diabetes.

As used herein, the term "pre-diabetes" refers to a condition or state in which some but not all of the symptoms, features or diagnostic criteria for diabetes are met. For example, in some pre-diabetes patients, the fasting blood glucose level is consistently elevated above what is considered normal levels, yet is not high enough to be diagnosed as diabetes. Thus, in some embodiments, pre-diabetes may also be known as "impaired fasting glucose."

Determination of blood glucose levels for use in determining need and/or parameters for CPX utilization may be carried out in any fashion as is generally known in the art. Many clinical methods exist for assaying blood sugar levels, including but not limited to, fasting blood sugar test, urine glucose test, two-hour postprandial blood sugar test, oral glucose tolerance test, intravenous glucose tolerance test, glycosylated hemoglobin test, self-monitoring of glucose levels via patient testing, and/or random blood sugar testing. The fasting blood sugar/blood glucose test is the most common test for initial assessment of the presence or risk for developing diabetes. The test requires that an individual abstains from eating for at least 8 hours prior to the test. Typically, up to 100 mg/dL is considered normal for a fasting blood glucose test. Subjects with levels between 100 mg/dL and 125 mg/dL are typically considered to have impaired fasting glucose, or be pre-diabetic, and subjects with levels that are 126 mg/dL or greater are typically considered diabetic. Through administration of ciclopirox to a subject, a fasting glucose level can be dropped to an improved level, for instance to a level of about 130 mg/dL or less, about 125 mg/dL or less, or about 100 mg/dL or less in some embodiments.

Typically, a glucose tolerance test is used for measuring blood sugar levels. Impaired glucose tolerance is generally diagnosed if the blood glucose level measured during a glucose tolerance test is in the range of 140 mg/dL (7.84 mM) to 199 mg/dL (11.1 mM). Diabetes is generally diagnosed if the measured blood glucose level is 200 mg/dL (11.2 mM) or higher. But, as physiological status fluctuates continually, no single glucose tolerance test is definitive, and treatment for reducing of blood glucose levels need not be predicated solely on the results of such testing.

Glucose levels can decrease by use of CPX in diabetic as well as in non-diabetic controls, which has led to the understanding that the anti-diabetic activity of CPX is also related to metabolic effects associated with the stress-induced by glucotoxicity. Indeed, assessment of insulin release in islets treated with CPX shows strong inhibition of insulin production triggered by high glucose. Considering the anti-diabetic action of CPX in mice this inhibition of insulin production is rather unexpected. Without wishing to be bound to any particular theory, it is believed that by inhibiting the production of insulin the β cells are less prone to develop ER stress that may compromise pancreatic function. This concept raises the possibility that besides modulating the outcome of the unfolded protein response, CPX can also regulate the efficiency of induction of the response. As shown below in the Examples section, assessment of the levels of the ER stress markers BiP, GRP94 and CHOP in islets cultured in high glucose-containing media shows that CPX can reduce the intensity of the unfolded protein response. In addition, a moderate suppression in the levels of intracellular insulin has also been found. This effect, however, can be less pronounced as compared to that recorded for the insulin released in the media. The fact that CPX can modestly suppress insulin expression in the cells but can potently inhibit its release from the cells suggests that CPX interferes more with insulin secretion than production. Considering that insulin accumulation has not been recorded during CPX treatment and also that ER stress was not induced but rather suppressed, this implies that CPX operates upstream of insulin production, reducing the islets' sensitivity to glucose. To that end, in mice, during diet-induced diabetes, β cells can retain their functionality and glucose homeostasis can be attained despite the fact that insulin production is compromised by the disease state.

Beneficially, administration of CPX treatment in vivo can produce a rapid response, which may imply additional levels at which CPX interferes with glucose homeostasis, beyond the promotion of islets' survival during glucose-induced stress of the ER.

Figure 1:
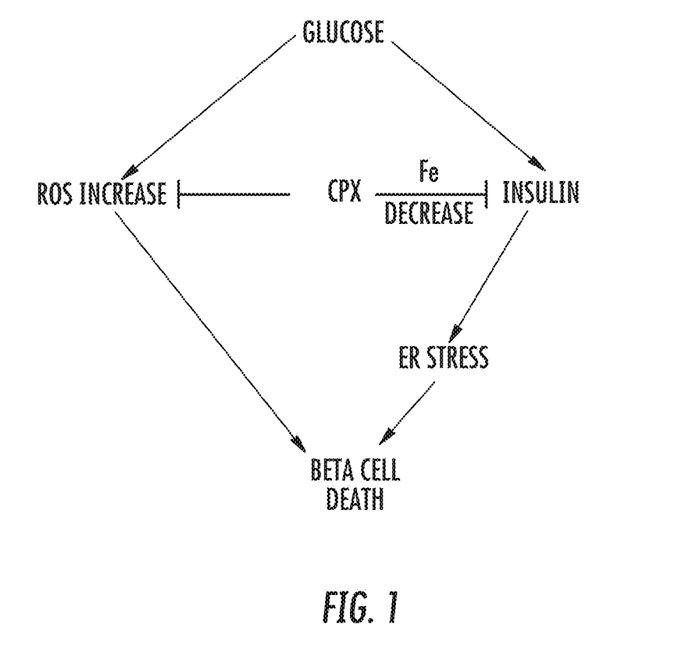
FIG. 1 is a diagrammatic depiction of the presumed role of CPX in regulating islets' survival by modulating insulin release.
Figure 2A:
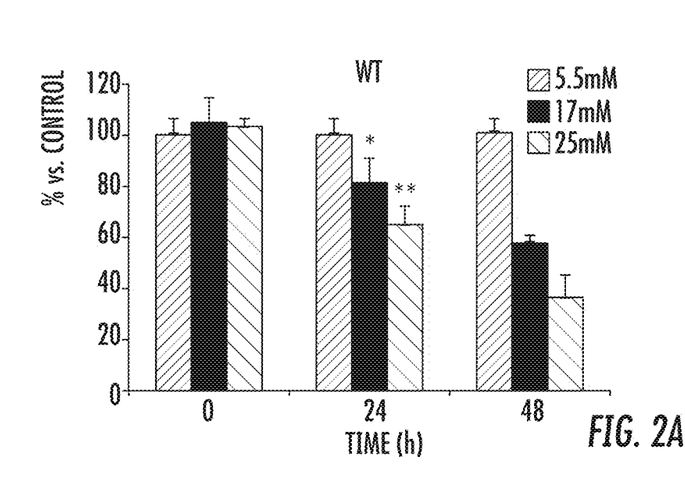
FIG. 2 illustrates survival of pancreatic islets cultured at increasing amounts of glucose for 24 h and 48 h including wild type islets (A), CHOP deficient islets (B), p53 deficient islets (C) and p21 deficient islets (D). *–$P<0.05$; **–$P<0.005$ Student's T test.
Figure 2B:
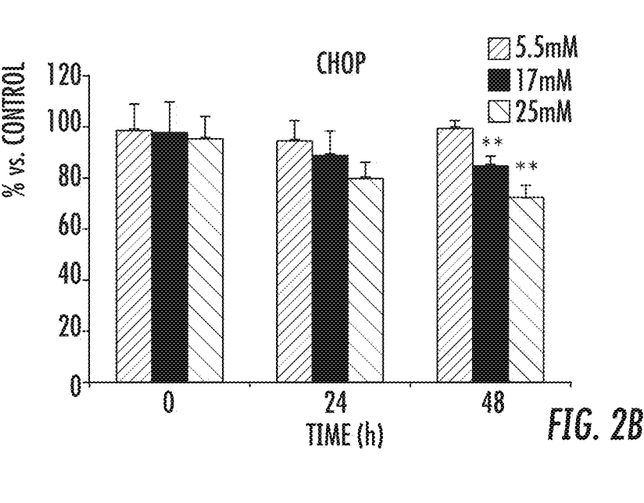
Figure 2C:
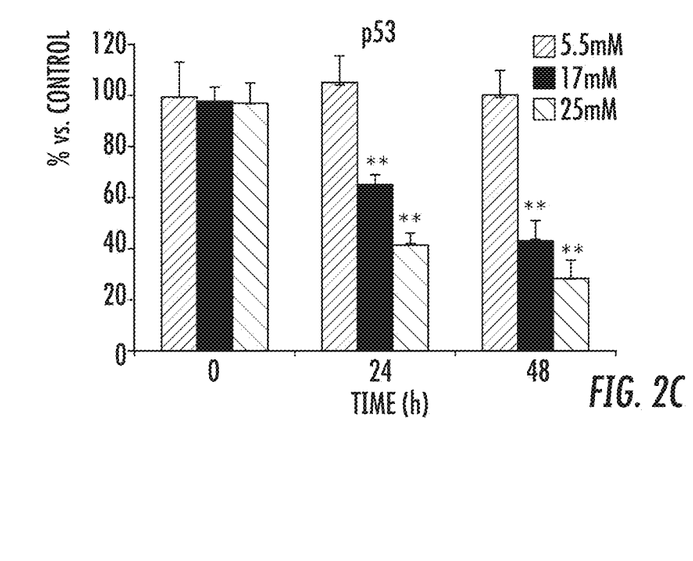
Figure 2D:
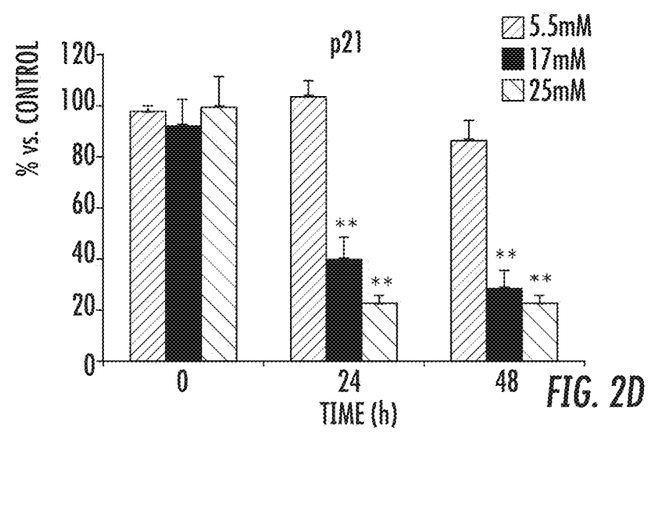

It is believed that the beneficial results of CPX administration are attained by converging mechanisms related both to the modulation of the p21-dependent sensitivity of β cells to ER stress-related apoptosis and by the regulation of the induction of unfolded protein response through inhibition of insulin release that constitutes a major stimulator of ER stress in β cells. These activities involve mechanisms that appear to be both β cell-specific, such as regulation of insulin production, and mechanisms that may operate in additional cell types also such as the alleviation of reactive oxygen species (ROS) production (FIG. 1). Thus, the beneficial activity of CPX may be not limited only to the management of diabetes, but also to other diseases associated with ER stress. Taking the in vivo and the in vitro findings together and as schematically illustrated in FIG. 1, it is believed that CPX promotes glucose homeostasis by multiple different mechanisms. Promotion of islets' survival is attained by p21-dependent mechanisms. However, in view the efficacy of CPX in p21-deficient mice, p21-independent mechanisms may also operate.

In accordance with the disclosed methods, CPX can be administered to a subject alone (e.g., as a purified compound), or as a component of a composition or medicament (e.g., in the manufacture of a medicament for the treatment of the disease). A composition can be formulated with a physiologically acceptable carrier or excipient to prepare a pharmaceutical composition. The carrier and composition can be sterile. The formulation can suit the mode of administration as is known.

Suitable pharmaceutically acceptable carriers can include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylase or starch, sugars such as mannitol, sucrose, or others, dextrose, magnesium stearate, talc, silicic acid, viscous paraffin, perfume oil, fatty add esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) that do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulations can include standard carriers such as pharmaceutical grades of mannitol, lactose, starch, magnesium stearate, polyvinyl pyrrolidone, sodium saccharine, cellulose, magnesium carbonate, etc.

The composition or medicament can be formulated in accordance with the routine procedures as a pharmaceutical composition adapted for administration to human beings. For example, in one embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

In some embodiments, provided compositions, including those provided as pharmaceutical formulations, comprise a liquid carrier such as but not limited to water, saline, phosphate buffered saline. Ringer's solution, dextrose solution, serum-containing solutions, Hank's solution, other aqueous physiologically balanced solutions, oils, esters and glycols.

CPX can be formulated in neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The CPX compound may be administered by any appropriate route. In some embodiments, the CPX can be administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, the CPX can be administered intravenously, orally, or by direct administration to a target tissue, such as muscle (e.g., intramuscular) or tumor (intratumorally), Alternatively, CPX can be administered by inhalation, parenterally, intradermally, transdermally, or transmucosally (e.g., orally or nasally). More than one route can be used concurrently, if desired.

In general, a composition can be administered in a therapeutically effective amount and/or according to a dosing regimen that is correlated with a particular desired outcome (e.g., with treating or reducing risk for diabetes).

Particular doses or amounts to be administered may vary, for example, depending on the nature and/or extent of the desired outcome, on particulars of route and/or timing of administration, and/or on one or more characteristics (e.g., weight, age, personal history, genetic characteristic, lifestyle parameter, severity of symptoms and/or level of risk of diabetes, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce blood glucose levels by about 5% or more, by about 10% or more, by about 25% or more, by about 50% or more, by about 75% or more, or by about 100% or more in some embodiments. By way of example, an appropriate dose or amount can be determined through use of one or more in vitro or in vivo assays to help identify desirable or optimal dosage ranges or amounts to be administered. For instance, through administration of ciclopirox to a subject, the blood glucose level in the subject can be reduced to a level of about 200 mg/dL or less or about 150 mg/dL or less in some embodiments.

In general, CPX can be administered in a therapeutically effective amount. As used herein, the term "therapeutically effective amount" is largely determined based on the total amount of the therapeutic agent contained in a pharmaceutical composition. Generally, a therapeutically effective amount is sufficient to achieve a meaningful benefit to the subject (e.g., treating, modulating, preventing and/or ameliorating the underlying lack of glucose homeostasis). In some particular embodiments, appropriate doses or amounts to be administered may be extrapolated from dose-response curves derived from in vitro or animal model test systems.

Therapeutically effective dosage amounts of CPX may be in varying amounts in various embodiments. In some embodiments, a therapeutically effective dosage amount can be, for example, about 0.001 mg/kg body weight to about 500 mg/kg body weight, about 0.01 mg/kg body weight to about 400 mg/kg body weight, about 1 mg/kg body weight to about 200 mg/kg body weight, or about 10 mg/kg body weight to about 1000 mg/kg body weight in some embodiments. The effective dose for a particular individual can be varied (e.g., increased or decreased) over time, depending on the needs of the individual. In some embodiments, the therapeutically effective amount described herein is provided in one dose. In some embodiments, a therapeutically effective amount described herein can be provided in one day. Alternatively, multiple doses can be provided in one day. For instance, CPX can be administered to a subject at an effective dose ranging from about 1 mg/kg/day to about 1,000 mg/kg/day, or at an effective dose ranging from about 1 mg/kg/day to about 500 mg/kg/day, for instance from about 10 mg/kg/day to about 500 mg/kg/day.

In some embodiments, a composition is provided as a pharmaceutical formulation. In some embodiments, a pharmaceutical formulation is or comprises a unit dose amount for administration in accordance with a dosing regimen correlated with achievement of the reduced incidence or risk of diabetes.

In some embodiments, a formulation comprising CPX can be administered as a single dose. In some embodiments, a formulation comprising CPX can be administered at regular intervals. Administration at an "interval," as used herein indicates that the therapeutically effective amount is administered periodically (as distinguished from a one-time dose). The interval can be determined by standard clinical techniques. In some embodiments, a formulation comprising CPX can be administered bimonthly, monthly, twice monthly, triweekly, biweekly, weekly, twice weekly, thrice weekly, daily, twice daily, every six hours, etc. Moreover, the administration interval for a single individual need not be a fixed interval, but can be varied over time, depending on the needs of the individual.

CPX can be administered to a subject alone or in combination with one or more known therapeutic agents (e.g., anti-diabetic medications) currently used for diabetes prophylaxis and treatment. For example, the anti-diabetic medication can include biguanides, thiazolidinediones, dual PPAR agonists, secretagogues including sulphonylureas, meglitinides/glinides (K+), incretin mimetics, DPP-4 inhibitors, insulin, insulin analogs or special formulations, alpha-glucosidase inhibitors, amylin or amylin analogues, SGLT2 inhibitors, Benfluorex, Tolrestat, and combinations thereof. In some embodiments, the known therapeutic agent(s) is/are administered according to its standard or approved dosing regimen and/or schedule. In some embodiments, the known therapeutic agent(s) can be administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

The present disclosure may be better understood with reference to the examples set forth below.

EXAMPLES

Testing Materials and Methods

Animals and Islets. Colonies of C57BI/6 mice were original purchased from the Jackson Laboratory (Bar Harbor, Me., USA). Animal care and experiments were carried out in accordance with the guidelines of the Animal Facilities recommendations.

Islet Isolation and Viability Assessment. Pancreatic islets were manually isolated from female C57BI/6 mice by the collagenase digestion method (Sigma-Aldrich; Li et al. 2009) and placed in a 96-well plate. The islets were incubated at 37° C. with 95% air and 5% $CO_2$. Islets were manually picked after dithizone (DTZ; Sigma Chemical Co) staining. Before experiments were performed, the islet cells were incubated with extracellular Krebs-Ringer (KR) solution (Sigma-Aldrich) and with increasing amounts of glucose for 24 h and 48 h. Islet cell viability was assessed using CellTiter 96 AQueous One Solution Cell Proliferation Assay from Promega (Madison, USA).

Western Blotting. The mouse islets were treated with CPX 20 µM for 24 h and lysed in RIPA buffer [50 mM Tris, pH 7.2; 150 mM NaCl; 1% sodium deoxycholate; 0.1% SDS; 1% Triton-X 100; 10 mM NaF; 1 mM $Na_3VO_4$; protease inhibitor cocktail (1:1000, Sigma, St. Louis, Mo.)] and were subjected to immunoblot analysis by standard methods. Proteins were resolved on a 10% SDS-PAGE and transferred to a nitrocellulose membrane (Bio-Rad, Hercules, Calif.). Membranes were probed overnight with GADD153 (F-168), sc-575 from Santa Cruz Biotechnology (1:50); p21 (F-5), sc-6246 from Santa Cruz Biotechnology (1:200); actin, clone C4 MAB1501 from Millipore (Billerica, Mass., USA) (1:2000); BiP antibody (cat. no. 3183) from Cell Signaling (Danvers, Mass., USA) (1:1000); GRP94 antibody (H-212), sc-11402 from Santa Cruz Biotechnology (1:500); insulin rabbit polyclonal H-86, sc-9168 from Santa Cruz Biotechnology (1:500) antibodies followed by incubation with horseradish peroxidase-conjugated (HRP) anti-mouse (1:10000), goat anti-rabbit IgG (1:10000, Santa Cruz biotechnology Inc., Santa Cruz, Calif., USA) for 1 hr. After incubation with enhanced chemiluminescence reagents (Santa Cruz biotechnology Inc.), membranes were analyzed using an Image J software for Windows.

In Vivo Analysis of Anti-Diabetic Effect of CPX. Mice were randomly grouped. A group of C57BI/6 mice 4-5 weeks old, were fed with either a solution of 10% sucrose and a diet containing 40% kcal as a high-fat diet (HFD; Open Source Diets (New Brunswick, N.J., USA) D12451, 40% calories/fat with free access to (10%) sweetened water (sucrose) or a control chow diet containing 10% of kcal as fat (low-fat diet) and drinking water with no added sucrose (control). Mice with a glucose concentration exceeding 180 mg/dL were considered diabetic, after 2 consecutive glucose measurements. The blood glucose levels were measured using an Accu-Check blood glucose monitor (Roche, Indianapolis, Ind., USA) using blood sample collected from the tail vein. Diabetic mice were treated with either treated daily for 20 days by oral gavages with CPX (25 mg/kg) prepared in a solution (4% ethanol, 5.2% Tween 80, and 5.2% PEG 400) or vehicle control. Pancreata were preserved in 10% buffered formalin for later histological examination.

Glucose Level Determination and Intraperitoneal Insulin Tolerance Test. Mice were fasted for 6 h. Glucose levels of mice were measured by an Accu-Chek Active meter (ROCHE) with blood sample obtained from the tail. For glucose tolerance, mice were injected i.p. with 2 g glucose/kg blood glucose was checked at different time points as indicated (at either 0, 30, 60, 90, 120, 160, 220 min.). For insulin resistance test, mice were injected intraperitoneally at a dose of 0.75 units/kg with human insulin (0.75 U/kg body weight; Sigma) at different time points as indicated, as for glucose tolerance after insulin injection and blood glucose was measured as described.

Immunostaining. Pancreatic tissue samples were fixed at 10% buffered formalin, processed a defined paraffin-embedding procedure before embedding in paraffin, sectioning into 4-µm tissue sections, and stained with hematoxylin and eosin by standard methods.

Measurement of Cellular ROS Production. Islets were incubated with KR buffer containing 0.01% (w/v) bovine serum albumin (BSA), 16 mM HEPES, and 2.8 mM glucose for 60 min at 37° C. ROS measurements were measured by using the DCFDA Cellular ROS Detection Assay Kit (Abcam/Mitosciences) in a 96-well dark microplate in accordance with the manufacturer's guidelines. Briefly, 30 islets were seeded into each well. On the day of the experiment, the islets were washed with 1×phosphate buffered saline and stained with 20 µM DCFH-DA in the dark for 30 min at 37° C. After incubation, DCFH-DA was removed, and the islets were washed with 1×buffer solution. Islets were seeded in a 96-well plate followed by high glucose alone or in combination with CPX glucose treatment and iron citrate alone or in combination with CPX treatment. Samples were analyzed using a Varioskan Flash micro-plate reader (Thermo-Scientific) with excitation wavelength at 485 nm and an emission wavelength at 535 nm. Tert-Butyl hydroperoxide (TBHP) was used as positive control.

Statistics. Statistical analysis was performed by the student's T test. Differences were considered significant when $P<0.05$ Example 1 p21-deficiency, p53-deficiency and CHOP-deficiency were explored with regard to how each affects sensitivity of pancreatic islets to diabetes. CHOP is a transcription factor that is induced during ER stress and mediates the pro-apoptotic activity of the unfolded protein response. CHOP deficiency is known to render mice resistant to diabetes and the suppression of p21 by CHOP during ER stress has been demonstrated.

As shown in FIG. 2, culture of wild type (wt) pancreatic islets at increasing amounts of glucose induced toxicity that was time-dependent (A). Consistently with the pro-apoptotic role of CHOP during ER stress, CHOP deficiency (B) conferred resistance since only culture at high glucose for 48 h caused significantly inhibited islet growth. In agreement with the protective role of p21 and p53 during the unfolded protein response, ablation of these cell cycle regulators sensitized islets to the cytotoxic effects of high glucose (C, D).

Figure 3:
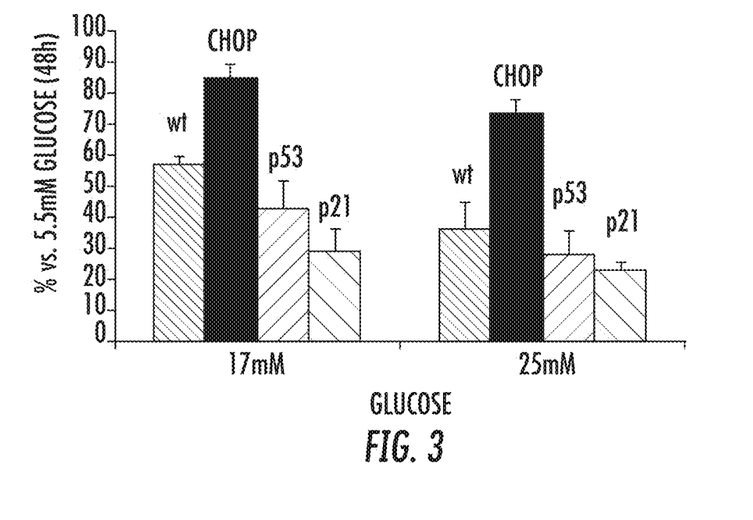
FIG. 3 illustrates the relative survival of wild type islets, CHOP deficient islets, p53 deficient islets, and p21 deficient islets in two different high glucose cultures expressed as % vs. survival at normal glucose.

As shown in FIG. 3, p21 conferred more potent pro-survival activity than p53 likely because the prosurvival action of the latter is masked by its concomitant pro-apoptotic activity. The fact that p21 ablation was the more potent sensitizer for glucotoxicity in islets implies that specific pharmacological stimulation of p21 activity may bear significant anti-diabetic value surpassing that reported earlier for nutlin-3a.

Example 2

Figure 4:
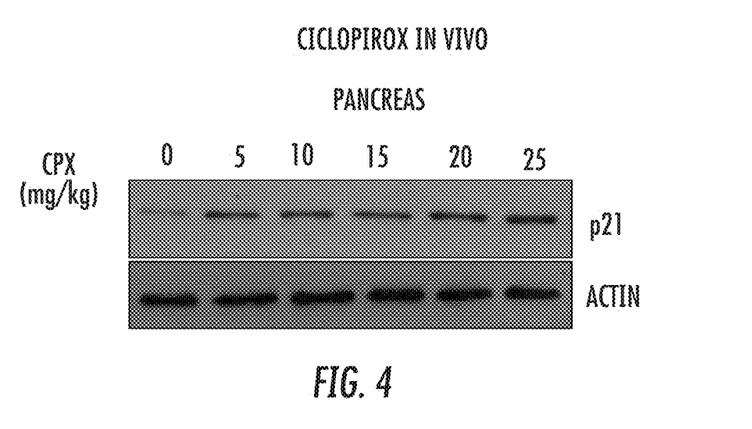
FIG. 4 illustrates p21 expression in the pancreas of mice that received CPX.

To determine if CPX treatment induces p21 levels in the pancreas, mice received orally CPX at 0-25 mg/kg daily for 5 days and the levels of p21 were assessed. As shown in FIG. 4, CPX administration from as low as 5 mg/kg effectively stimulated the expression of p21 in the pancreas of wild type mice. Actin levels were used as a positive control.

Figure 5A:
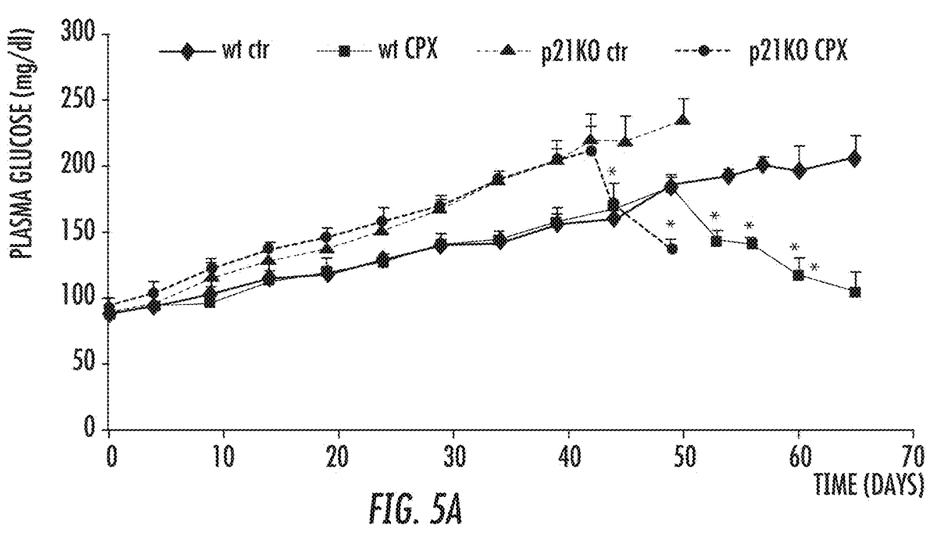
FIG. 5 illustrates fasting glucose levels of wild type and p21 knock out (p21 KO) mice after CPX administration (A) and fasting glucose levels of wild type mice receiving normal diet and CPX (B).
Figure 5B:
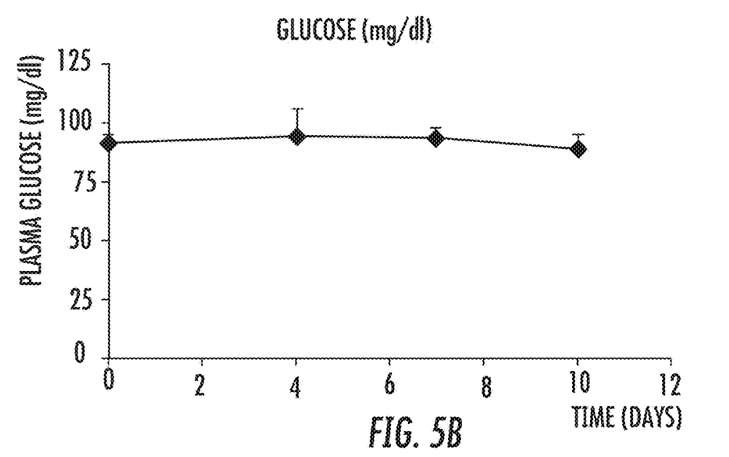

Subsequently, the consequences for daily CPX administration were explored in glucose homeostasis of wt mice that became diabetic by receiving high fat diet as described combined with glucose at 10% in their drinking water. As control, a standard chow diet was used containing 10% of kcal as fat (low-fat diet) and drinking water with no added sucrose (control). The experimental treatment was initiated about 50 days after initiation of the diabetes-inducing diet, when fasting glucose levels were about 185 mg/dl. As shown in FIG. 5, CPX at 25 mg/kg daily effectively improved glucose homeostasis causing reduction of blood glucose levels (A).

In order to evaluate the requirement of p21 for CPX activity, the experiment was repeated in p21-deficient mice. The p21-deficient mice, consistent with earlier observations, were more sensitive to diet-induced diabetes than wt controls and exhibited fasting glucose levels of 180 mg/kg as early as 35 days after special diet administration (FIG. 5 at A). Following, they received CPX similar to the controls. Surprisingly, notwithstanding the fact that they exhibited a delayed response, p21-deficient mice also responded significantly to CPX in terms of glucose regulation (FIG. 5 at A).

In order to test if the antidiabetic activity of CPX was elicited only in diabetic mice or in non-diabetic mice as well, plasma glucose levels were assessed in wt mice that were receiving normal diet in combination with CPX. As shown in FIG. 5 at B, no reduction of glucose levels was recorded suggesting that CPX is effective only under diabetic conditions.

Figure 6A:
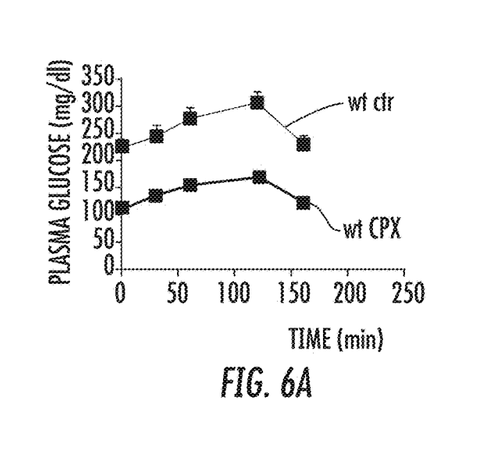
FIG. 6 illustrates glucose tolerance (A) and insulin sensitivity (B) of diabetic mice treated with saline as control or CPX.
Figures 6B, 7B, 7C:
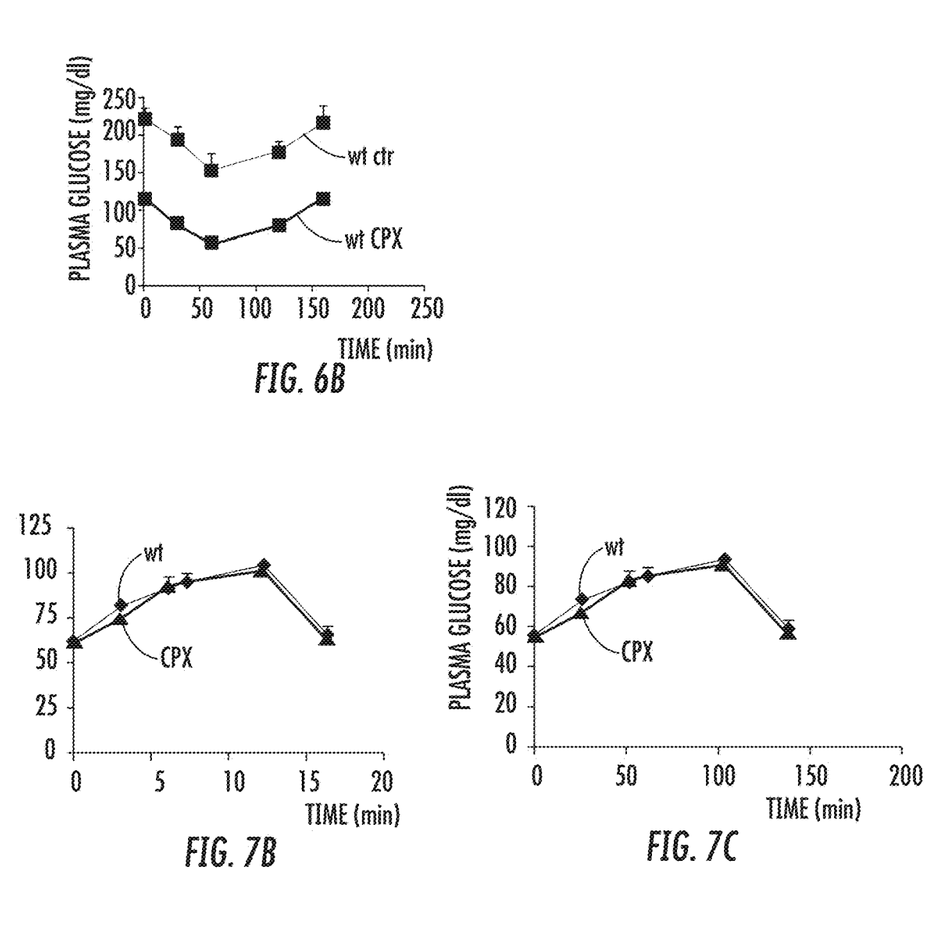
FIG. 7 illustrates fasting glucose (A) glucose tolerance (B) and insulin sensitivity (C) of wild type mice receiving normal diet and CPX or saline.

As shown in FIG. 6, glucose tolerance (A) and insulin sensitivity (B) tests suggested that CPX restored the response of diabetic mice to acute administration of glucose. Diabetic mice with similar levels of fasting glucose were selected between experimental groups.

Figure 7A:
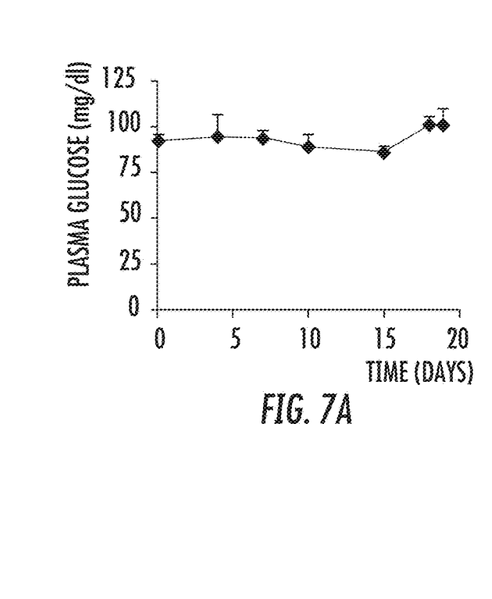
Figure 8A:
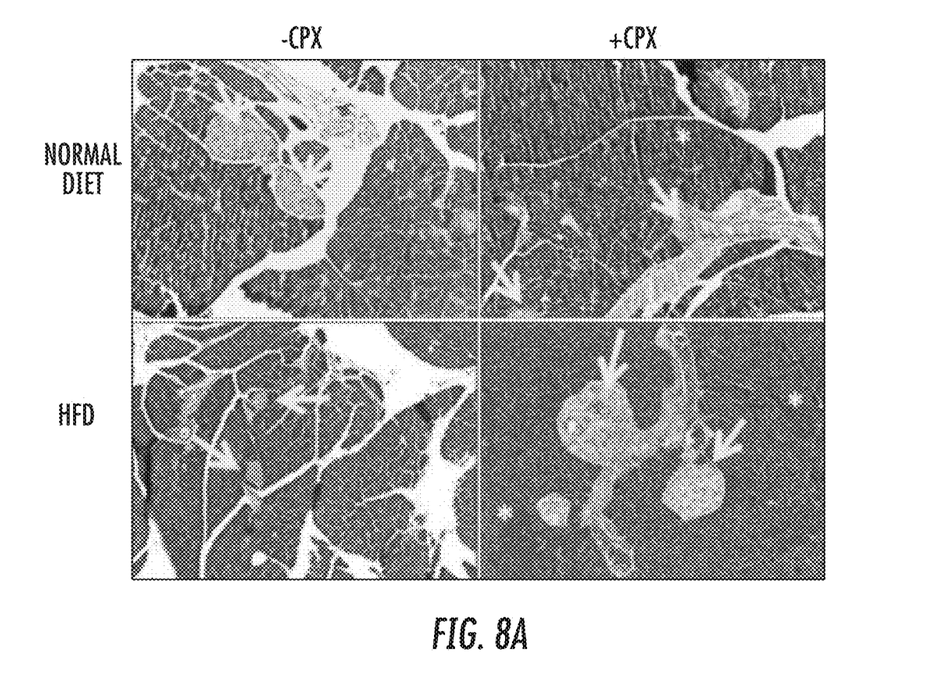
Figure 8B:
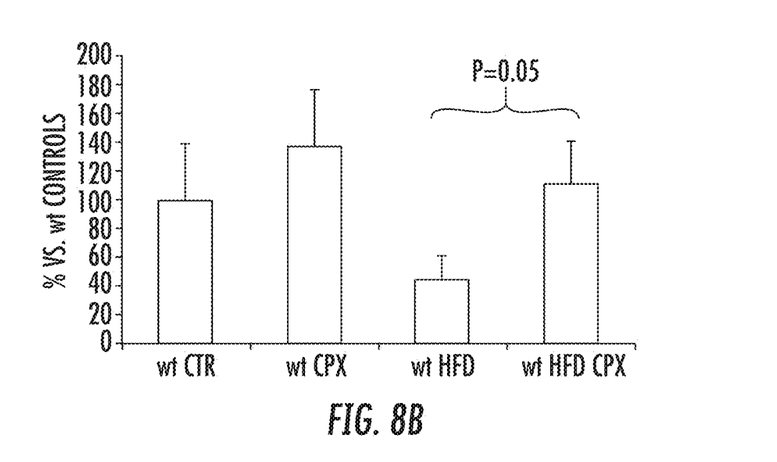

The effects of CPX in glucose homeostasis were limited to the diabetic mice as demonstrated by the fact that glucose levels in wt mice were not affected by CPX administration as shown in FIG. 7 with regard to fasting glucose levels (A), glucose tolerance (B), and insulin sensitivity (C). Furthermore, as shown in FIG. 8, histological analysis of pancreata from both diabetic and wt mice treated with CPX as illustrated (A, wt—upper panel, diabetic—lower panel) and shown graphically (B) suggested that islet numbers increased significantly only in the diabetic mice, but not in the non-diabetic mice.

Example 3

To examine the mechanism by which CPX promotes glucose homeostasis and in view of its p21 stimulating activity and the beneficial effects of p21 expression in β cell survival during glucotoxic stress as illustrated in FIG. 2 and FIG. 3, CPX protection of islets from glucotoxicity by p21-dependent mechanisms was evaluated.

Figure 9A:
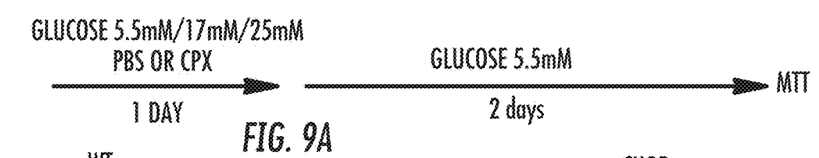
FIG. 9 illustrates an experimental design of how islet survival was assessed in the presence of CPX.
Figure 10A:
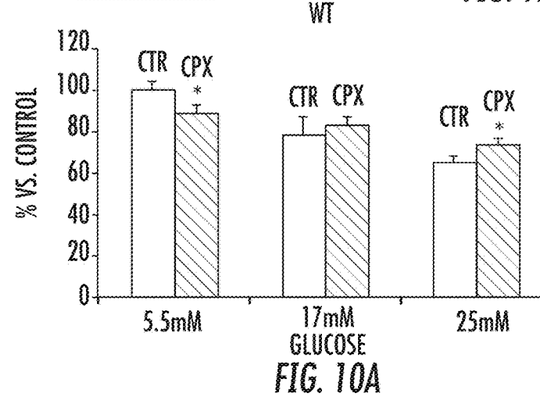
FIG. 10 illustrates islet survival in relation to genotype at various glucose concentrations in the presence or absence of CPX including wild type islets (A), CHOP deficient islets (B), p53 deficient islets (C) and p21 deficient islets (D). –$P<0.05$; **–$P<0.005$ Student's T test.
Figure 10B:
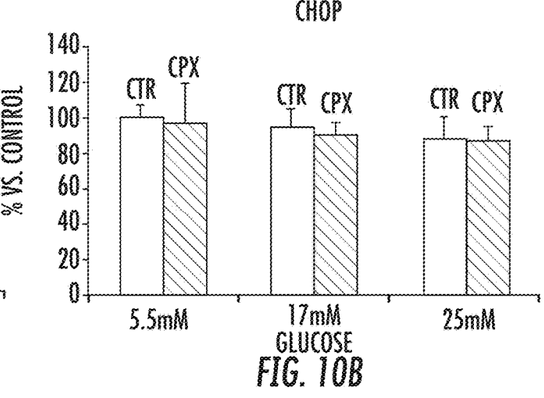
Figure 10C:
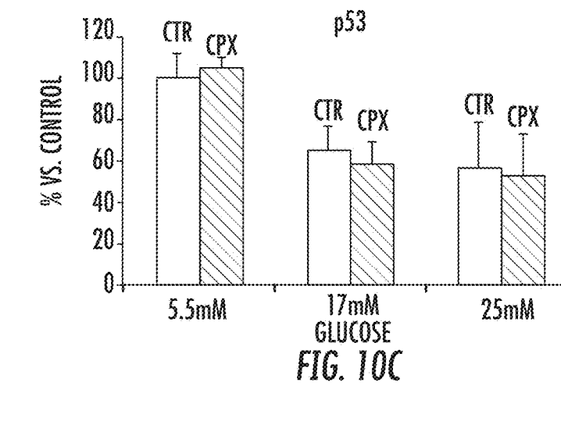
Figure 10D:
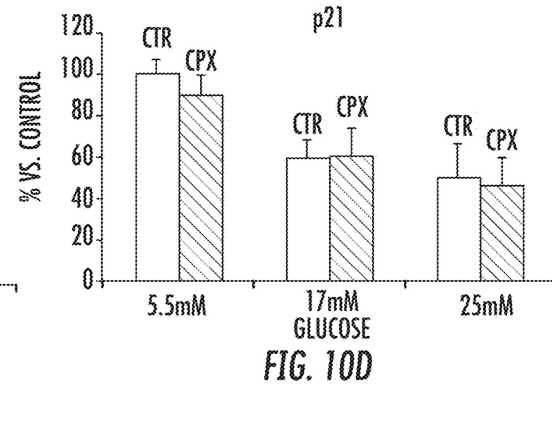

Islets from wt, p21-deficient, p53-deficient and CHOP-deficient mice were exposed to CPX at 20 µM for 24 h under increasing glucose amounts in the culture media, then they were let to recover for 48 h in normal glucose-containing media and their survival was assessed (FIG. 9). The 48 h recovery in normal media was deemed necessary because CPX, by inducing p21 expression would inflict cell cycle arrest in islets masking the effects of glucotoxicity. Indeed, CPX treatment of wt islets under normal glucose significantly inhibited islet growth. As shown in FIG. 10, despite this cytostatic effect in wt islets under normal glucose (A), CPX protected wt but not p21-deficient animals from glucotoxicity (D) suggesting that intact p21 expression is required for the pro-survival activity of CPX. A similar trend was also found for p53 (FIG. 10 at C). The p21-stimulatory activity of CPX in the islets is also p53-independent. This observation suggests that p53 deregulation may alleviate the pro-survival activity of CPX by alternative mechanisms. Consistently with its pro-apoptotic role during ER stress CHOP ablation conferred resistance of islets to glucotoxicity (FIG. 10 at B).

Example 4

Figure 11A:
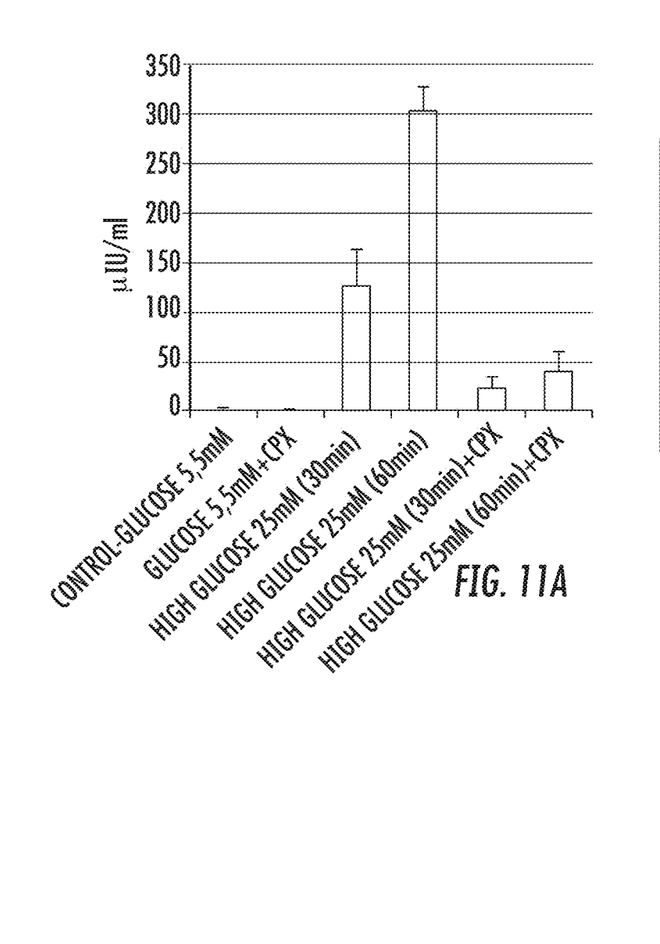
FIG. 11 illustrates insulin release in wild type and p21-deficient islets following glucose stimulation and treated with CPX (A) and expression of insulin, CHOP, GRP94 and BiP in wild type and p21-deficient islets treated with high glucose alone or in combination with CPX (B). Actin levels were assessed as loading control. High glucose experiment was performed in triplicate.
Figure 11B:
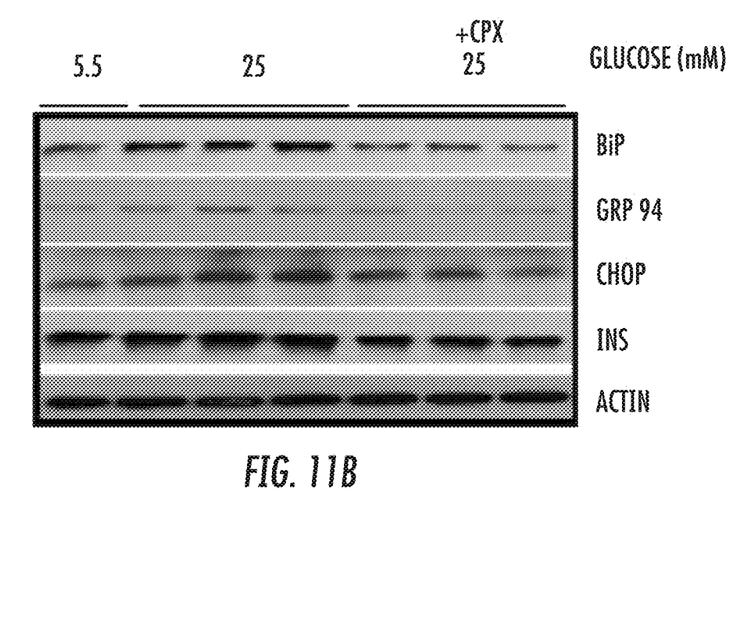

In order to understand better how CPX operates in β cells, it was tested to determine if it affected the efficiency by which insulin is produced following glucose stimulation. As shown in FIG. 11 CPX suppressed the release of insulin (A). In view of the antidiabetic activity of CPX in vivo, the inhibition of insulin release appears contradictory. Thus, it was hypothesized that reduced insulin secretion may be linked to reduced ER stress and blunted unfolded protein response, which in turn could explain in the long run the increased survival and functionality of the animals that received CPX. To test this hypothesis, islets were exposed to CPX and high glucose and the levels were tested of chaperones BiP, GRP94 and CHOP that reflect the intensity of the UPR. As shown in FIG. 11, CPX alleviated the levels of BiP, GRP94 and CHOP in the wt islets suggesting that the execution of the UPR was compromised (A). In line with these observations and consistently with the insulin levels in the media (FIG. 11 at A) were also the levels of insulin in the β islets (FIG. 11 at B).

Figure 12A:
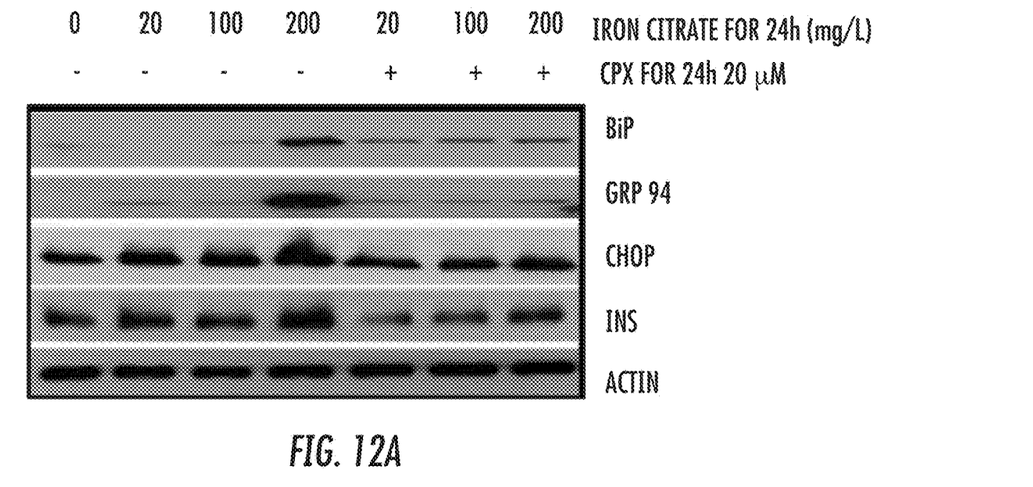
FIG. 12 illustrates the effects of iron citrate and ciclopirox at the indicated concentrations in insulin, BiP, GRP94 and CHOP levels in islets in culture (A). Actin levels were assessed as loading control. High glucose experiment was performed in triplicates. At B is illustrated the effect of CPX in ROS production (in arbitrary units, AU) that was triggered by high glucose (Glu) or iron citrate (Fe). TBHP was used as positive control for ROS production. The results shown reflect the average of 2 independent experiments each of which was performed in triplicates. *.P<0.05.
Figure 12B:
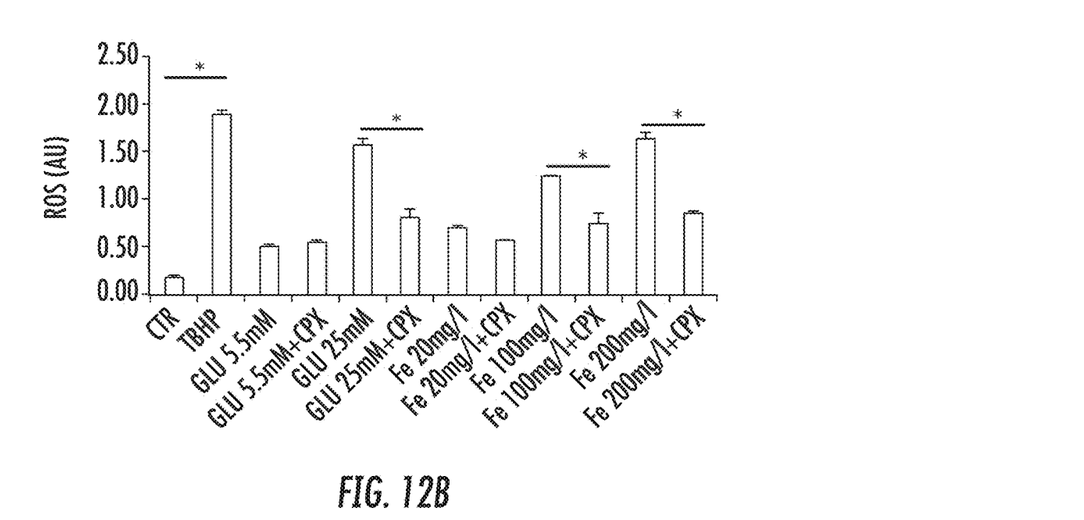

While modulation of insulin release by CPX constitutes a challenging mechanism by which CPX may affect ER stress, how CPX regulates insulin expression remains obscure. Being an iron chelator, it is conceivable that CPX modulates insulin production by adjusting the levels of bioavailable iron in the islets. To test this hypothesis, islets were exposed to iron citrate, alone or combined with CPX, and the levels were recorded of chaperones BiP, GRP94 and CHOP, as well as of insulin. As shown in FIG. 12, increasing amounts if iron citrate triggered insulin production and induced ER stress-markers BiP, GRP94 and CHOP (A). Concomitant exposure though of islets with CPX compromised the effects of iron citrate in insulin production and ER stress induction (A). In addition to ER stress, CPX was also a potent inhibitor of ROS that were produced by culture of islets to iron citrate and high glucose (B).

This written description uses examples to disclose the invention, including the best mode, and also to enable any person skilled in the art to practice the invention, including making and using any devices or systems and performing any incorporated methods. One scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method of modulating glucose homeostasis comprising administering to a subject in need thereof ciclopirox, wherein the subject has been diagnosed with diabetes and wherein the administration of the ciclopirox reduces the blood glucose level in the subject to about 200 mg/dL or less.

2. The method of claim 1, wherein the diabetes is type I diabetes, type II diabetes, or gestational diabetes.

3. The method of claim 1, wherein the subject has been diagnosed with pre-diabetes.

4. The method of claim 1, wherein the ciclopirox is administered daily, twice a week, weekly, once every two weeks, once every three weeks, monthly, or at a variable interval.

5. The method of claim 1, wherein the ciclopirox is administered intravenously, intradermally, orally, by inhalation, transdermally (topical), subcutaneously, and/or transmucosally.

6. The method of claim 1, wherein the ciclopirox is administered at a dose of from about 0.001 mg/kg body weight to about 500 mg/kg body weight.

7. The method of claim 1, wherein the ciclopirox is administered at a daily dosage of from about 1 mg/kg/day to about 1,000 mg/kg/day.

8. The method of claim 1, wherein the administration of the ciclopirox results in a reduction in fasting blood glucose levels in the subject as compared to a control.

9. The method of claim 1, wherein the administration of the ciclopirox reduces the fasting glucose level in the subject to about 130 mg/dL or less.

10. The method of claim 1, wherein the ciclopirox is administered in combination with an anti-diabetic medication.

11. The method of claim 10, wherein the anti-diabetic medication comprises biguanides, thiazolidinediones, dual PPAR agonists, secretagogues, meglitinides/glinides (K+), incretin mimetics, DPP-4 inhibitors, insulin, insulin analogs or special formulations, alpha-glucosidase inhibitors, amylin, or amylin analogues, SGLT2 inhibitors, Benfluorex, Tolrestat, and combinations thereof.

12. The method of claim 1, wherein the subject is about 60 years of age or older.

13. The method of claim 10, wherein the anti-diabetic medication comprises sulphonylureas.

14. A method of modulating glucose homeostasis comprising administering to a subject in need thereof ciclopirox, wherein the ciclopirox is administered intravenously, intradermally, orally, by inhalation, subcutaneously, and/or transmucosally and wherein the ciclopirox is administered daily, twice a week, weekly, once every two weeks, once every three weeks, monthly, or at a variable interval.

15. The method of claim 14, wherein the ciclopirox is administered at a dose of from about 0.001 mg/kg body weight to about 500 mg/kg body weight.

16. A method of modulating glucose homeostasis comprising administering to a subject in need thereof ciclopirox, wherein the ciclopirox is administered at a dose of from about 0.001 mg/kg body weight to about 500 mg/kg body weight, and wherein the ciclopirox is administered in combination with an anti-diabetic medication.

17. The method of claim 16, wherein the ciclopirox is administered at a daily dosage of from about 1 mg/kg/day to about 1,000 mg/kg/day.

18. The method of claim 16, wherein the ciclopirox is administered intravenously, intradermally, orally, by inhalation, transdermally (topical), subcutaneously, and/or transmucosally.

* * * * *